(12) United States Patent
Zhou et al.

(10) Patent No.: US 11,963,970 B2
(45) Date of Patent: Apr. 23, 2024

(54) PREPARATION METHOD OF GINSENG COMPOSITION WITH HIGH GINSENOSIDE BIOAVAILABILITY

(71) Applicants: Jiangnan University, Wuxi (CN); Standard Foods (China) Co., Ltd, Suzhou (CN); Le Bonta Wellness Co., Ltd, Shanghai (CN)

(72) Inventors: Peng Zhou, Wuxi (CN); Changshu Liu, Suzhou (CN); Tao Yang, Wuxi (CN); Chang Liu, Wuxi (CN); Yaowei Liu, Wuxi (CN); Zikuan Zhao, Wuxi (CN); Jianguo Liu, Suzhou (CN); Kexin Li, Shanghai (CN)

(73) Assignees: JIANGNAN UNIVERSITY, Wuxi (CN); STANDARD FOODS (CHINA) CO., LTD, Suzhou (CN); LE BONTA WELLNESS CO., LTD, Shanghai (CN)

( * ) Notice: Subject to any disclaimer, the term of this patent is extended or adjusted under 35 U.S.C. 154(b) by 0 days.

(21) Appl. No.: 18/367,577

(22) Filed: Sep. 13, 2023

(65) Prior Publication Data

US 2023/0414643 A1    Dec. 28, 2023

Related U.S. Application Data

(63) Continuation of application No. PCT/CN2023/078780, filed on Feb. 28, 2023.

(30) Foreign Application Priority Data

Mar. 11, 2022   (CN) .......................... 202210235378.4

(51) Int. Cl.
| | | |
|---|---|---|
| A61K 36/00 | (2006.01) |
| A61K 8/63 | (2006.01) |
| A61K 8/73 | (2006.01) |
| A61K 8/9789 | (2017.01) |
| A61K 31/704 | (2006.01) |
| A61K 36/258 | (2006.01) |
| A61K 47/40 | (2006.01) |

(52) U.S. Cl.
CPC .............. *A61K 31/704* (2013.01); *A61K 8/63* (2013.01); *A61K 8/738* (2013.01); *A61K 8/9789* (2017.08); *A61K 36/258* (2013.01); *A61K 47/40* (2013.01); *A61K 2236/15* (2013.01)

(58) Field of Classification Search
None
See application file for complete search history.

(56) References Cited

FOREIGN PATENT DOCUMENTS

| CN | 102920762 A | * | 2/2013 |
|---|---|---|---|
| CN | 102920762 A | | 2/2013 |
| CN | 109985079 A | | 7/2019 |
| CN | 111450132 A | | 7/2020 |
| CN | 111973642 A | | 11/2020 |
| CN | 112034114 A | | 12/2020 |
| CN | 114558043 A | | 5/2022 |

* cited by examiner

*Primary Examiner* — Qiuwen Mi
(74) *Attorney, Agent, or Firm* — IPRO, PLLC

(57) ABSTRACT

The present disclosure discloses a preparation method of ginseng composition with high ginsenoside bioavailability. The composition is composed of ginseng powder of 250 meshes or more and β-cyclodextrin, and the mass ratio of the ginseng powder to the β-cyclodextrin is 1:0.05. Results show that when β-cyclodextrin is used as a solid dispersant and added to the 1000-mesh ginseng powder at a mass ratio of 5%, the total dissolution amount is maximum; and furthermore, animal experiments (SD rats) show that the area under the plasma drug concentration-time curve ($AUC_{0-48\,h}$) after 48 h of ginseng powder ingestion is maximum, indicating that in-vivo bioavailability of the ginseng powder is the highest. The method of this application can effectively inhibit the aggregation of the ultra-finely pulverized 1000-mesh ginseng powder by adding the β-cyclodextrin, thus significantly improving the total dissolution amount of ginsenoside.

4 Claims, 3 Drawing Sheets

PREPARATION METHOD OF GINSENG COMPOSITION WITH HIGH GINSENOSIDE BIOAVAILABILITY

TECHNICAL FIELD

The present disclosure relates to a preparation method of a ginseng composition with high ginsenoside bioavailability, belonging to the technical field of food processing.

BACKGROUND

Ginsenosides are triterpenoids composed of hydrophobic (extremely low polarity) aglycones and hydrophilic (higher polarity) sugar moieties. Based on the different structures of the aglycones, the aglycones can be divided into three categories: two categories of dammarane-type tetracyclic triterpenoid saponins (protopanaxadiol-type saponins, protopanaxatriol-type saponins) and one category of oleanolic acid-type pentacyclic triterpenoid saponins. Ginsenoside is the most important active ingredient in ginseng that exerts important physiological functions, such as anti-aging, anti-inflammation, anti-oxidation, anti-fatigue, anti-diabetic, anti-cancer, protecting the nervous system, and improving immunity. Although the ginsenosides have good pharmacological effects, they have large molecular weight, poor water solubility, and low extraction rate, resulting in a low absorption rate and bioavailability in the form of ginseng powder.

In the patent "Enteric-coated *Panax Notoginseng* Saponins and its Preparation Method (CN102579536A)", *Panax notoginseng* saponins are subjected to ultrafine pulverization, and mixed with starch or microcrystalline cellulose or dextrin to prepare particles, and then mixed with magnesium stearate to prepare an enteric-coated *Panax Notoginseng* Saponins tablets. The *Panax notoginseng* saponins in this patent need to be separated and purified, and the dextrin plays a role of embedding the purified *Panax notoginseng* saponins, thereby improving the solubility of the *Panax notoginseng* saponins. However, the method is cumbersome in steps and complicated in process, and requires separation and purification of the saponins from plants and then preparation into tablets with several food additives. The present disclosure is based on an experimental result: as the particle size of the ginseng powder decreases (from 80-mesh to 250-mesh), the total dissolution amount of ginsenoside increases continuously; however, once exceeding 250 meshes, the total dissolution amount of ginsenoside has no significant changes. Based on this, adding β-cyclodextrin to the ultra-finely pulverized 1000-mesh ginseng powder can effectively increase the total dissolution amount of the ginsenoside. The present disclosure uses the ginseng powder as a raw material without further separation and purification of ginsenosides. As a solid dispersant, the β-cyclodextrin increases the electrostatic repulsion among the ginseng powders by adsorption onto the surface of the ginseng powder, thus avoiding the aggregation of the ultra-finely pulverized 1000-mesh ginseng powder, and further achieving the purpose of improving the dissolution rate and bioavailability of the ginsenosides.

SUMMARY

Technical Problem

The purpose of the present disclosure is to provide a method for increasing the total dissolution amount and bioavailability of ginsenoside by adding β-cyclodextrin into ginseng powder. This disclosure provides an easy, efficient, minimally processed, and environment-friendly method to produce ginseng powders with ultrafine and uniform particle size, and high dissolution rate and bioavailability of ginsenoside. Therefore, the method has great value in the application of food and medicine.

Technical Solution

The first objective of the present disclosure is to provide a ginseng composition with high ginsenoside bioavailability, which is composed of ginseng powder of 250 meshes or more and β-cyclodextrin, where the mass ratio of the ginseng powder to the β-cyclodextrin is 1:0.05.

As a preferred example of the present disclosure, the ginseng powder of 250 meshes or more is prepared from 80-mesh ginseng powder by dry ultrafine pulverization and step-by-step sieving.

The second objective of the present disclosure is to provide a method for preparing the aforementioned ginseng composition with high ginsenoside bioavailability, which includes the following steps:
(1) performing dry ultrafine pulverization on ginseng powder of a certain meshes by using a planetary ball mill, and sieving step by step to obtain ginseng powder of 250 meshes or more; and
(2) adding β-cyclodextrin to the ginseng powder of 250 meshes or more, with the mass ratio of the ginseng powder to the β-cyclodextrin being 1:0.05, so as to obtain a ginseng composition.

As a preferred example of the present disclosure, the parameters of the planetary ball mill in step (1) are as follows: the grinding speed is 200-400 rpm, and the grinding time is 15-45 min.

The third objective of the present disclosure is to provide a method for extracting ginsenoside from ginseng, which includes the following steps:
(1) performing dry ultrafine pulverization on ginseng powder of a certain meshes by using a planetary ball mill, and sieving step by step to obtain ginseng powder of 250 meshes or more;
(2) adding β-cyclodextrin to the ginseng powder of 250 meshes or more, with the mass ratio of the ginseng powder to the β-cyclodextrin being 1:0.05, so as to obtain a ginseng composition; and
(3) enabling the ginseng composition to be sequentially subjected to simulated oral digestion, simulated gastric digestion, and simulated intestinal digestion via a static in vitro digestion experimental model to obtain a final digesta, where the total dissolution amount of ginsenoside per unit of ginseng mass in the final digesta is not less than 42 mg/g.

As a preferred example of the present disclosure, the simulated oral digestion is implemented by the steps: adding 2 g of the ginseng composition and 3 mL of water to 4 mL of simulated oral digestive juice preheated to 37° C., oscillating by using a vortex oscillator for mixing well, and controlling the concentration of α-amylase in the final simulated oral digesta to be 75 U/mL, where
a preparation method of the simulated oral digestive juice includes the steps: mixing 25 μL of a 44.1 g/L CaCl$_2$ stock solution, 0.5 mL of an α-amylase solution and 0.475 mL of water, and keeping the mixture in a constant temperature water bath at 37° C. for 2 min.

As a preferred example of the present disclosure, the simulated gastric digestion is implemented by the steps:

adding a simulated oral digesta to 8 mL of simulated gastric digestive juice preheated to 37° C., and incubating the mixture in a constant temperature oscillating water bath kettle or thermostatic incubator at 37° C. for 2 h, where a preparation method of the simulated gastric digestive juice includes the steps: adjusting the pH to 3.0 with a 1.0 mol/L HCl solution, recording the volume of the HCl solution used, sequentially adding 5 μL of a 44.1 g/L $CaCl_2$ stock solution and 0.5 mL of a pepsin solution, making the enzyme activity of pepsin in the final simulated gastric digestive juice reach 2000 U/mL, and finally adding water to make the total volume reach 20 mL.

As a preferred example of the present disclosure, the simulated intestinal digestion is implemented by the steps: adding a simulated gastric digesta to 8.5 mL of simulated intestinal digestive juice preheated to 37° C., and incubating the mixture in a constant temperature oscillating water bath kettle at 37° C. for 2 h in an oscillating manner, where a preparation method of the simulated intestinal digestive juice includes the steps: adjusting the pH to 7.0 with a 1.0 mol/L NaOH solution, recording the volume of the NaOH solution used, sequentially adding 2.5 mL of a bovine bile salt solution, 25 μL of a 44.1 g/L $CaCl_2$ stock solution, 5 mL of a pancreatin solution, and water, ensuring that the concentration of bovine bile salt in the simulated intestinal digestion stage is 10 mmol/L, and the enzyme activity of pancreatin in the simulated intestinal digestion stage is 100 U/mL, and adding water to make the total volume of intestinal digestive substances reach 40 mL.

The fourth objective of the present disclosure is to provide application of the aforementioned ginseng composition with high ginsenoside bioavailability in the preparation of food, medicine or cosmetics.

Beneficial Effects (1) The method capable of improving the total dissolution amount of the ginsenoside by adding the β-cyclodextrin in the present disclosure has the advantages of being short in processing time, energy-saving, easy to operate, pollution-free, free from by-products, fine in powder particle size, uniform in distribution, high in total dissolution amount of the ginsenoside, and the like. The method capable of improving the total dissolution amount of the ginsenoside by adding the β-cyclodextrin in the present disclosure is unique. It is found in a large number of experiments that the ginseng powder with a mesh number greater than 250 will aggregate into agglomerates, restricting the dissolution of ginsenosides. Therefore, the present disclosure employs β-cyclodextrin to be compounded with the ginseng powder with a specific mesh number to improve the total dissolution amount of the ginsenoside. Research has found that when the mesh number of the ginseng powder is greater than 250, for example, the mesh number of the ginseng powder is 1000, the optimized mass ratio of the ginseng powder to the β-cyclodextrin is 1:0.05. At this time, the total dissolution amount of the ginsenoside per unit mass of ginseng is the highest (greater than 42 mg/g). The total dissolution amount of ginsenosides in ginseng powder without adding β-cyclodextrin is lower than 37 mg/g under the same conditions, and this value increased by 16.2% or above when the ginseng powder is compounded with β-cyclodextrin.

(2) The present disclosure has screened many formulations and found that: only by adopting the technical solution of adding β-cyclodextrin as a solid dispersant at a mass ratio of the ginseng powder to the β-cyclodextrin of 1:0.05 in the present disclosure, the total dissolution amount of the ginsenoside can be significantly increased (greater than 42 mg/g). However, if other types of dispersants, such as pregelatinized starch, maltodextrin or lactose, are used, the total dissolution amount of the ginsenoside is lower than 39 mg/g. Besides, the total dissolution amount of the ginsenoside is lower than 37 mg/g when the mass ratio of the ginseng powder to the β-cyclodextrin is not at 1:0.05. The result of Example 1 shows that there is no significant difference in the total dissolution amount of the ginsenoside from ginseng powder with a mesh number greater than 250 without addition of the β-cyclodextrin, and the total dissolution amount of the ginsenoside is lower than 38 mg/g.

(3) The results of animal experiments show that there is a significant difference in the area under the curve in 0-48 h ($AUC_{0-48\,h}$) of plasma concentration-time of ginsenoside corresponding to 80-mesh, 250-mesh and 1000-mesh ginseng powder as well as 1000-mesh ginseng powder added with 5% (w/w) β-cyclodextrin. It is further confirmed that adding 5% (w/w) β-cyclodextrin to the 1000-mesh ginseng powder is helpful to increase the total dissolution amount of the ginsenoside, which can effectively improve the bioavailability of ginsenosides.

DETAILED DESCRIPTION

Figure 1:
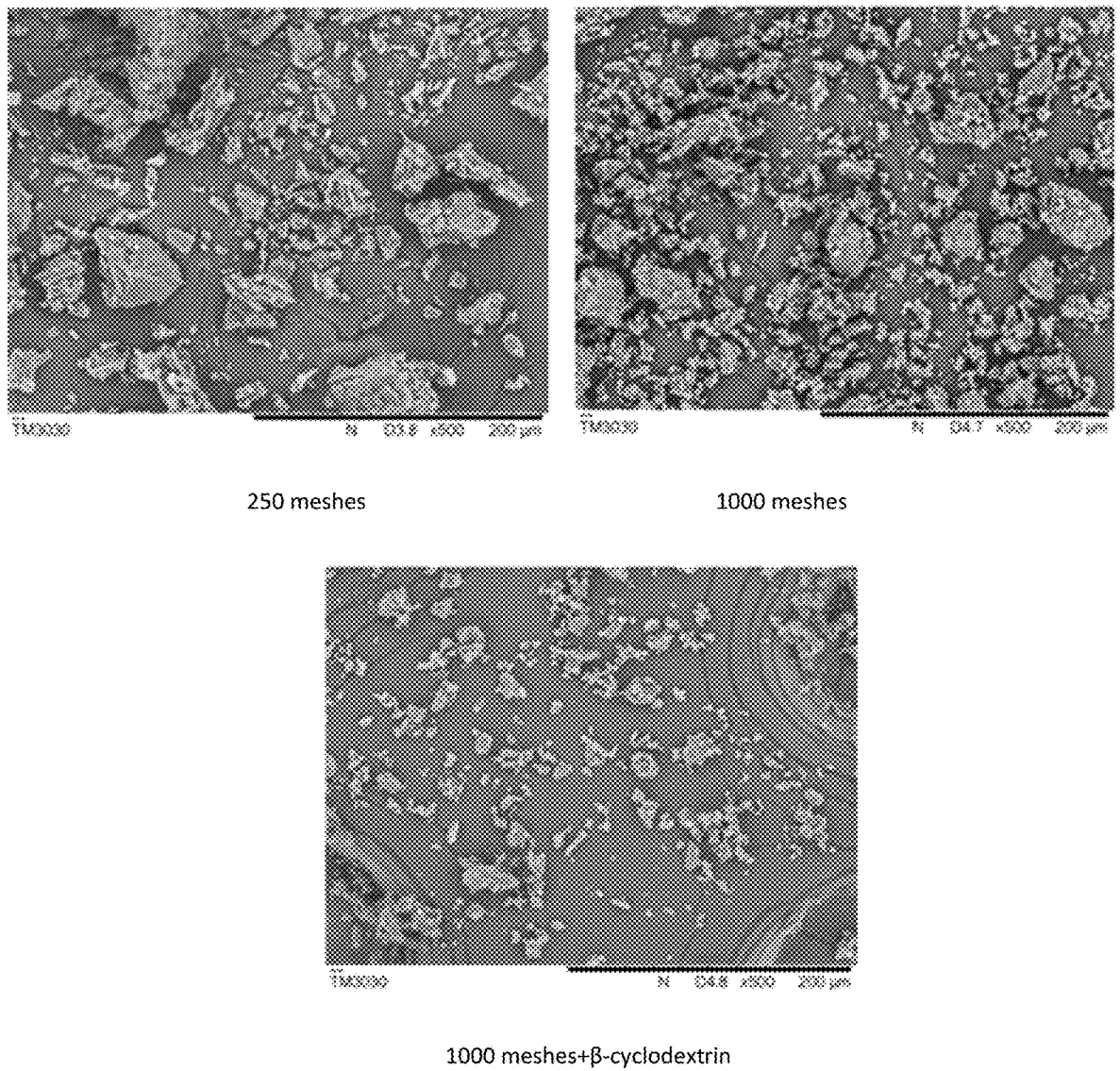
FIG. 1 shows aggregation diagrams of 250-mesh and 1000-mesh ginseng powder, and a dispersion diagram of 1000-mesh ginseng powder added with β-cyclodextrin.

The present disclosure will be further described in detail below in conjunction with the examples, but it should be noted that the scope of the present disclosure is not limited by these examples.

The specific steps of performing digestion experiments (including oral digestion, gastric digestion, and intestinal digestion) via a static in vitro digestion experimental model in the examples and comparative examples of the present disclosure were described below.

Simulated oral digestion: 5 g of a water-powder mixture (containing 2 g of a powder sample and 3 mL of water) was added to 4 mL of simulated oral digestive juice preheated to 37° C., the mixture was mixed well by using a vortex oscillator, and the concentration of α-amylase in a final simulated oral digesta was controlled to be 75 U/mL. A preparation method of the simulated oral digestive juice includes the steps: mixing 25 µL of a 44.1 g/L $CaCl_2$ stock solution, 0.5 mL of an α-amylase solution and 0.475 mL of water, and keeping the mixture in a constant temperature water bath at 37° C. for 2 min.

Simulated gastric digestion: after the simulated oral digestion, sample was added to 8 mL of simulated gastric digestive juice preheated to 37° C., and the obtained mixture was incubated in a constant temperature oscillating water bath kettle or thermostatic incubator at 37° C. for 2 h. A preparation method of the simulated gastric digestive juice includes the steps: adjusting the pH to 3.0 with a 1.0 mol/L HCl solution, recording the volume of the HCl solution used, sequentially adding 5 µL of a 44.1 g/L $CaCl_2$ stock solution and 0.5 mL of a pepsin solution, making the enzyme activity of pepsin in the final simulated gastric digestive juice reach 2000 U/mL, and finally adding water to make the total volume reach 20 mL.

Simulated intestinal digestion: a simulated gastric digesta obtained by sequentially performing the simulated oral digestion and simulated gastric digestion on the sample to be tested was added to 8.5 mL of simulated intestinal digestive juice preheated to 37° C., and the mixture was incubated in a constant temperature oscillating water bath kettle at 37° C. for 2 h in an oscillating manner. A preparation method of the simulated intestinal digestive juice includes the steps: adjusting the pH to 7.0 with a 1.0 mol/L NaOH solution, recording the volume of the NaOH solution used, sequentially adding 2.5 mL of a bovine bile salt solution, 25 µL of a 44.1 g/L $CaCl_2$ stock solution, 5 mL of a pancreatin solution, and water, ensuring that the concentration of bovine bile salt in the simulated intestinal digestion stage is 10 mmol/L, and the enzyme activity of pancreatin in the simulated intestinal digestion stage is 100 U/mL, and adding water to make the total volume of intestinal digestive substances reach 40 mL.

High performance liquid chromatography was used to determine the total dissolution amount of ginsenoside per unit of ginseng mass in the final digesta obtained by performing digestion experiments (including oral digestion, gastric digestion, and intestinal digestion) on different samples to be tested via the static in vitro digestion experimental model. The determination conditions are TSKgel ODS-80™ (4.6 mm×250 mm, 5 µm) chromatographic column, and mobile phase: acetonitrile (A) and water (B); gradient elution is performed, and an elution procedure is shown in Table 1; and the injection volume is 10 µL, the flow rate is 1.0 mL/min, the column temperature is 25° C., the detection time is 130 min, and the ultraviolet detection wavelength is 203 nm.

TABLE 1

Mobile Phase Proportion Change Table

| Time (min) | Acetonitrile (%) | Ultrapure water (%) |
|---|---|---|
| 0 | 22.0 | 78.0 |
| 25.00 | 22.0 | 78.0 |
| 35.00 | 32.5 | 67.5 |
| 65.00 | 34.0 | 66.0 |
| 66.00 | 42.0 | 58.0 |
| 114.00 | 98.0 | 2.0 |
| 119.00 | 98.0 | 2.0 |
| 120.00 | 22.0 | 78.0 |
| 130.00 | 22.0 | 78.0 |

Example 1

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside 80-mesh ginseng powder that was not subjected to ultrafine pulverization was used as a control sample, and digestion experiments (including oral digestion, gastric digestion, and intestinal digestion) were performed on the obtained 80, 160, 250, 350, and 1000-mesh ginseng powder via a static in vitro digestion experimental model, so that final digesta were obtained.

(3) Determination of Total Dissolution Amount of Ginsenoside

Figure 2:
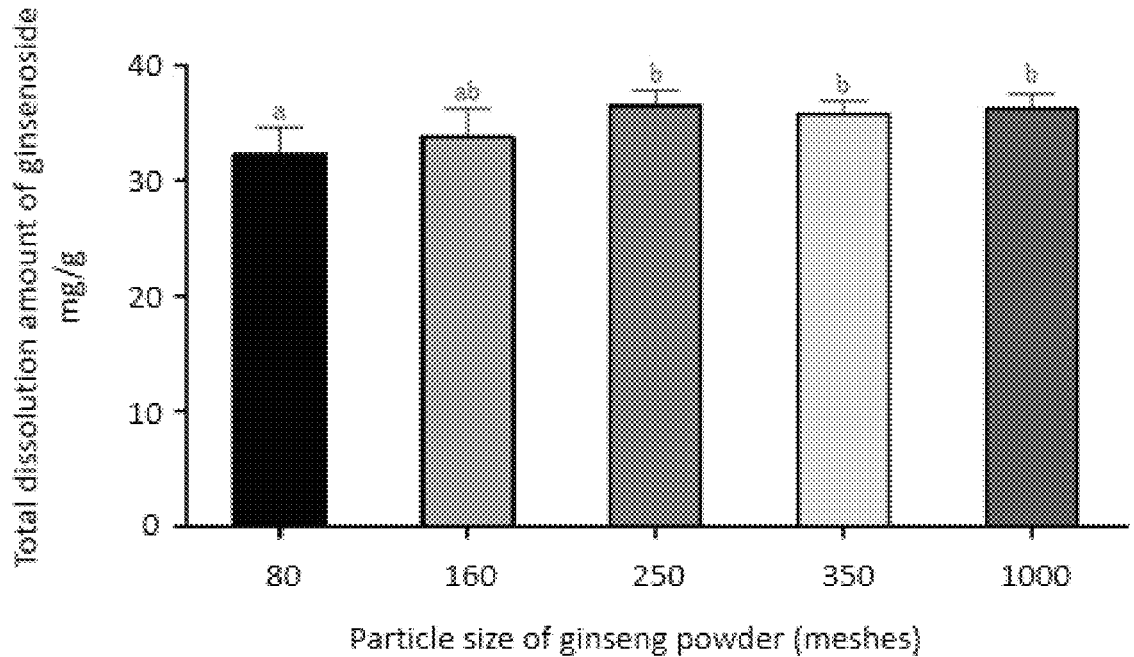
FIG. 2 shows the total dissolution amounts of ginsenoside in the final digesta obtained by performing digestion experiments (including oral digestion, gastric digestion, and intestinal digestion) on ginseng powder with different particle sizes via a static in vitro digestion experimental model in Example 1.

High performance liquid chromatography was used to determine the total dissolution amounts of ginsenoside per unit of ginseng mass in the final digesta of the ginseng powder with different mesh numbers (FIG. 2).

The results showed that with the decrease of the particle size of ginseng powder, the total dissolution amount of ginsenoside increased continuously from the 80-mesh ginseng powder to the 250-mesh ginseng powder, but after the mesh number of the ginseng powder exceeded 250, the total dissolution amount of the ginsenoside had no significant change.

In order to find out the factors that limit the further increase of the total dissolution amount of the ginsenoside, the microstructures of 250 and 1000-mesh ginseng powder were observed. The results are shown in FIG. 1. The present disclosure has found that the ginseng powder will aggregate into agglomerates after the particle size reaches a certain level, so that the particle size of the aggregated ginseng powder is almost the same as that of the 250-mesh ginseng powder, which affects the dissolution of the ginsenoside.

Example 2

On the basis of Example 1, in the ginsenoside extraction process of step (2), 3-cyclodextrin was added to the ginseng powder at a specific ratio.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

β-cyclodextrin was added to the 1000-mesh ginseng powder, and the mass ratio of the ginseng powder to the β-cyclodextrin was enabled to be 1:0.05, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

Figure 3:
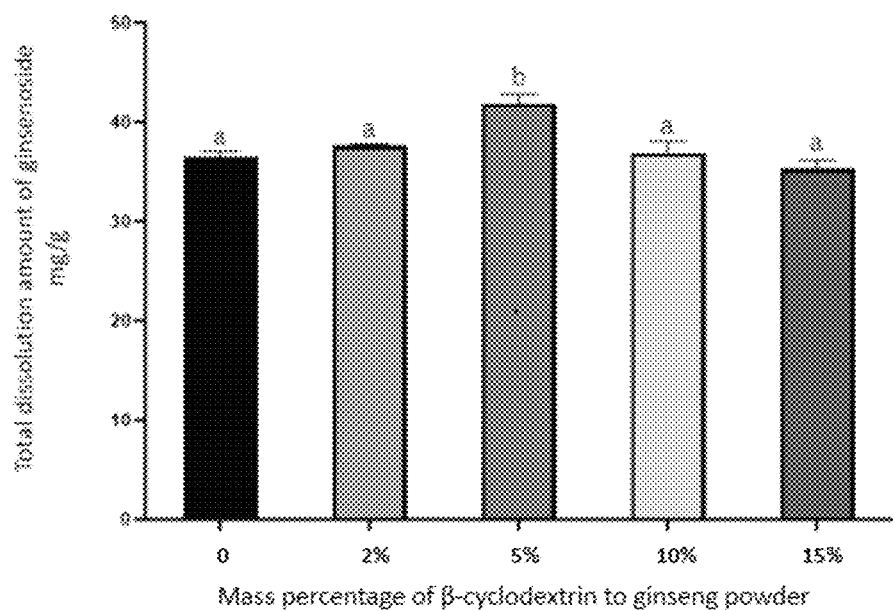
FIG. 3 shows the total dissolution amounts of ginsenoside in the final digesta obtained by performing digestion experiments (including oral digestion, gastric digestion, and intestinal digestion) via the static in vitro digestion experimental model when 0-15% (w/w) β-cyclodextrin is added to the 1000-mesh ginseng powder in Example 2 and Comparative Examples 1-4.

High performance liquid chromatography was used to determine the total dissolution amount of ginsenoside in the final digesta. The result is shown in FIG. 3.

The dispersion diagram of the 1000-mesh ginseng powder added with the R-cyclodextrin in this example is shown in FIG. 1.

Comparative Example 1 No β-Cyclodextrin Added

Referring to Example 2, the only difference was that the mass ratio of ginseng powder to β-cyclodextrin was 1:0.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

β-cyclodextrin was added to the 1000-mesh ginseng powder, and the mass ratio of the ginseng powder to the β-cyclodextrin was enabled to be 1:0, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

High performance liquid chromatography was used to determine the total dissolution amount of ginsenoside in the final digesta. The result is shown in FIG. 3.

Comparative Example 2 the Mass Ratio of Ginseng Powder to β-Cyclodextrin being 1:0.02

Referring to Example 2, the only difference was that the mass ratio of ginseng powder to β-cyclodextrin was 1:0.02.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

β-cyclodextrin was added to the 1000-mesh ginseng powder, and the mass ratio of the ginseng powder to the β-cyclodextrin was enabled to be 1:0.02, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

High performance liquid chromatography was used to determine the total dissolution amount of ginsenoside in the final digesta. The result is shown in FIG. 3.

Comparative Example 3 the Mass Ratio of Ginseng Powder to β-Cyclodextrin being 1:0.1

Referring to Example 2, the only difference was that the mass ratio of ginseng powder to β-cyclodextrin was 1:0.1.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

β-cyclodextrin was added to the 1000-mesh ginseng powder, and the mass ratio of the ginseng powder to the β-cyclodextrin was enabled to be 1:0.1, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

High performance liquid chromatography was used to determine the total dissolution amount of ginsenoside in the final digesta. The result is shown in FIG. 3.

Comparative Example 4 the Mass Ratio of Ginseng Powder to β-Cyclodextrin being 1:0.15

Referring to Example 2, the only difference was that the mass ratio of ginseng powder to β-cyclodextrin was 1:0.15.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

β-cyclodextrin was added to the 1000-mesh ginseng powder, and the mass ratio of the ginseng powder to the β-cyclodextrin was enabled to be 1:0.15, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

High performance liquid chromatography was used to determine the total dissolution amount of ginsenoside in the final digesta. The result is shown in FIG. 3.

FIG. 3 shows the total dissolution amounts of ginsenoside in the final digesta obtained by performing digestion experiments (including oral digestion, gastric digestion, and intestinal digestion) via the static in vitro digestion experimental model when 0-0.15 (w/w) β-cyclodextrin is added to the 1000-mesh ginseng powder in Example 2 and Comparative Examples 1-4. By comparison, it is found that when the mesh number of the ginseng powder is greater than 250, for example, the mesh number of the ginseng powder is 1000, the optimized mass ratio of the ginseng powder to the β-cyclodextrin is 1:0.05. At this time, the total dissolution amount of the ginsenoside per unit mass of ginseng is the highest (greater than 42 mg/g). Compared with ginseng powder not compounded with β-cyclodextrin, which has the total dissolution amount of ginsenoside per unit mass of ginseng not higher than 37 mg/g under the same conditions, the ginseng powder compounded with the β-cyclodextrin has the total dissolution amount of ginsenoside increased by 16.2% or above.

Comparative Example 5 Other Types of Dispersants

Referring to Example 2, the only difference was that the β-cyclodextrin was replaced by pregelatinized starch, maltodextrin, and lactose.

(1) Preparation of Ginseng Powder

A planetary ball mill was used to perform dry ultrafine pulverization on 80-mesh ginseng powder under the premise of adjusting the grinding speed (to 200-400 rpm), the grinding time (to 15-45 min), and the proportion of large and small magnetic beads (to 1:1, v/v or w/w), and the product was sieved step by step to obtain 80, 160, 250, 350, and 1000-mesh ginseng powder.

(2) Extraction of Ginsenoside

Pregelatinized starch (or maltodextrin, or lactose) was added to the 1000-mesh ginseng powder, and the mass ratio of the ginseng powder to the pregelatinized starch (or maltodextrin, or lactose) was enabled to be 1:0.05, so that a ginseng composition was obtained. The ginseng composition with a total mass of 2 g was used as a sample to be tested, and digestion experiments (including oral digestion, gastric digestion, and intestinal digestion) were performed on the sample to be tested via a static in vitro digestion experimental model, so that a final digesta was obtained.

(3) Determination of Total Dissolution Amount of Ginsenoside

High performance liquid chromatography was used to determine the total dissolution amount of ginsenoside in the final digesta. The result is shown in FIG. 4.

Figure 4:
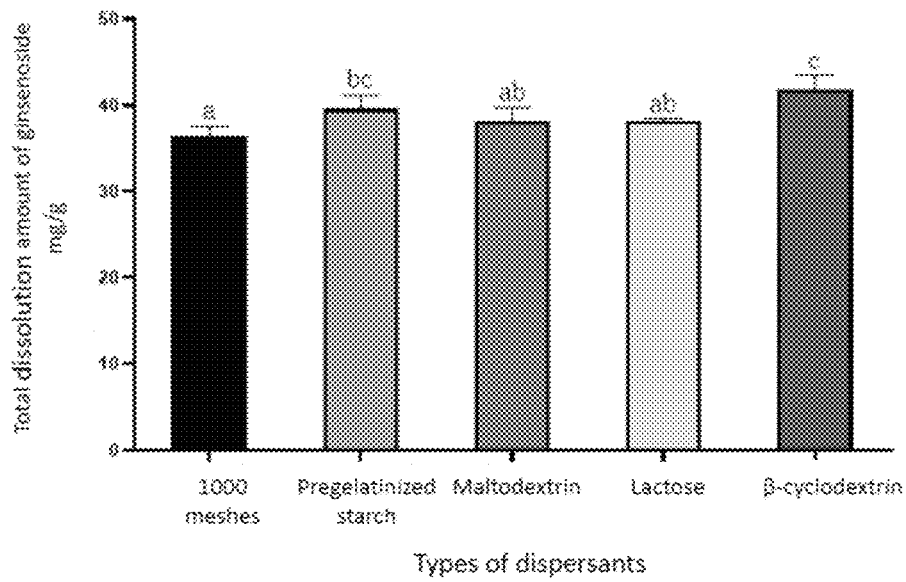
FIG. 4 shows the total dissolution amounts of ginsenoside from 1000-mesh ginseng powder and from 1000-mesh ginseng powder added with 5% (w/w) different dispersants in Example 2 and Comparative Example 5.

FIG. 4 shows the total dissolution amounts of ginsenoside in the final digesta obtained by performing digestion experiments (including oral digestion, gastric digestion, and intestinal digestion) via the static in vitro digestion experimental model when 0.05 (w/w) different types of dispersants are added to the 1000-mesh ginseng powder in Example 2 and Comparative Example 5. By comparison, it is found that although the pregelatinized starch, maltodextrin and lactose can also increase the total dissolution amounts of ginsenoside to a certain extent, they were not higher than 39 mg/g. The improvement effect of β-cyclodextrin in the present disclosure is the best, significantly superior to those of other types of dispersants.

To sum up, the present disclosure has screened many formulations and found that: only by adopting the technical solution of adding β-cyclodextrin as a solid dispersant and making the mass ratio of the ginseng powder to the β-cyclodextrin preferably being 1:0.05 in the present disclosure, the total dissolution amount of the ginsenoside (greater than 42 mg/g) can be significantly increased. However, if other types of dispersants, such as pregelatinized starch, maltodextrin or lactose, are selected to be added, the total dissolution amount of the ginsenoside is not higher than 39 mg/g. If not in the proportion according to the present disclosure, for example, even if the β-cyclodextrin is added, the total dissolution amount of the ginsenoside is not higher than 37 mg/g when the mass ratio of the ginseng powder to the β-cyclodextrin is too high or too low. The result of Example 1 shows that there is no significant difference in the total dissolution amount of the ginsenoside from ginseng powder with a mesh number greater than 250 without addition of the β-cyclodextrin, and the total dissolution amount of the ginsenoside is lower than 38 mg/g.

Therefore, it can be seen from the above examples and comparative examples that: after the 80-mesh ginseng powder is subjected to the process of dry ultrafine pulverization, adding a solid dispersant to the ginseng powder with a mesh number greater than 250 can significantly increase the total dissolution amount of ginsenoside. The key technical means is as follows: the solid dispersant is β-cyclodextrin, and the mass ratios of ginseng powder to β-cyclodextrin is 1:0.05. Under this condition, the total dissolution amount of ginsenoside in the final digesta obtained by performing digestion experiments (including oral digestion, gastric digestion, and intestinal digestion) via the static in vitro digestion experimental model is the highest, which has great market promotion value.

Example 3

Figure 5:
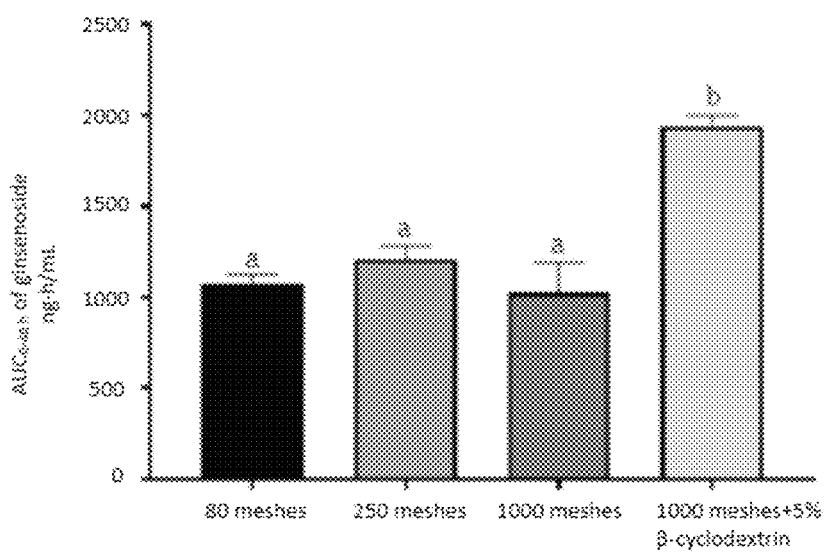
FIG. 5 shows areas under the plasma drug concentration-time curve in 0-48 h ($AUC_{0-48\,h}$) of ginsenoside in Example 3.

Sprague Dawley (SD) rats were gavaged with 80-mesh, 250-mesh, and 1000-mesh ginseng powder as well as 1000-mesh ginseng powder added with 0.05 (w/w) β-cyclodextrin. Specifically, the gavage composition was a water-powder mixture (containing 2 g ginseng powder/ginseng powder added with a dispersant, and 3 mL of water), the gavage concentration is 0.6 g/kg, and the gavage volume is 0.1 mL/10 g of rat body weight. The blood of the rats within 0-48 h was collected by a tail-reduced blood collection method, the plasma concentration of ginsenoside in the blood of the SD rats was determined by an ultra-high performance liquid chromatography-mass spectrometry (UPLC-MS) (see J. B. Chen, M. J. Li, L. X. Chen, Y. F. Wang, S. S. Li, Y. W. Zhang, L. Zhang, M. J. Song, C. Liu, M. Hua and Y. S. Sun, Effects of processing method on the pharmacokinetics and tissue distribution of orally administered ginseng, J Ginseng Res, 2018, 42, 27-34.), and the area under the curve in 0-48 h ($AUC_{0-48\ h}$) of plasma concentration-time of ginsenoside was calculated. The results are shown in FIG. 5.

The results of animal experiments show that there are significant differences in the area under the curve in 0-48 h ($AUC_{0-48\ h}$) of plasma concentration-time of ginsenoside corresponding to 80-mesh, 250-mesh and 1000-mesh ginseng powder as well as 1000-mesh ginseng powder added with 0.05 (w/w) β-cyclodextrin. It is further confirmed that adding the 0.05 (w/w) β-cyclodextrin to the 1000-mesh ginseng powder is helpful to increase the total dissolution amount of the ginsenoside, which can effectively improve the bioavailability of the ginsenoside.

What is claimed is:

1. A ginseng composition consisting of:
   1000-mesh dry ginseng powder, and
   a dry solid dispersant that is β-cyclodextrin, wherein the ginseng powder and β-cyclodextrin are uniformly mixed together, with a mass ratio of the ginseng powder to the β-cyclodextrin of 1:0.05 (w/w), and wherein the 1000-mesh dry ginseng powder is produced by ultrafine pulverization of 80-mesh dry ginseng powder by ball mill, followed by stepwise sieving to obtain uniform 1000-mesh dry ginseng powder.

2. The ginseng composition according to claim 1, produced by a process comprising the following steps:

dry ultrafine pulverizing ginseng powder with a planetary ball mill, and sieving step by step to obtain 1000-mesh ginseng powder; and adding β-cyclodextrin to the 1000-mesh ginseng powder, with the mass ratio of the ginseng powder to the β-cyclodextrin being 1:0.05 (w/w).

3. The ginseng composition according to claim 2, wherein the parameters of the planetary ball mill are as follows: a grinding speed of 200 rpm to 400 rpm, and a grinding time is 15 of 15 minutes to 45 minutes.

4. A food, medicine, or cosmetic containing the ginseng composition according to claim 1.

* * * * *